(12) United States Patent
Mazor et al.

(10) Patent No.: US 6,556,652 B1
(45) Date of Patent: Apr. 29, 2003

(54) MEASUREMENT OF CRITICAL DIMENSIONS USING X-RAYS

(75) Inventors: Isaac Mazor, Haifa (IL); Boris Yokhin, Nazareth Illit (IL); Amos Gvirtzman, Moshav Zippori (IL)

(73) Assignee: Jordan Valley Applied Radiation Ltd., Migdal Ha'Emek (IL)

( * ) Notice: Subject to any disclaimer, the term of this patent is extended or adjusted under 35 U.S.C. 154(b) by 99 days.

(21) Appl. No.: 09/635,212

(22) Filed: Aug. 9, 2000

(51) Int. Cl.⁷ .............................................. G01N 23/201
(52) U.S. Cl. ............................................ 378/86; 378/71
(58) Field of Search ........................ 378/86, 146, 147, 378/149, 84, 85, 87, 89, 90, 70, 81, 71

(56) References Cited

U.S. PATENT DOCUMENTS

| | | | | |
|---|---|---|---|---|
| 4,989,226 A | * | 1/1991 | Woodbury et al. | 378/145 |
| 5,619,548 A | * | 4/1997 | Koppel | 378/70 |
| 5,740,226 A | | 4/1998 | Komiya et al. | |
| 6,041,098 A | * | 3/2000 | Touryanski et al. | 378/70 |
| 6,226,349 B1 | * | 5/2001 | Schuster et al. | 378/84 |

OTHER PUBLICATIONS

Hayashi et al., "Refracted X–Rays Propagating Near the Surface under Grazing Incidence Condition", *Spectrochimica Acta*, Part B 54, 1999, pp. 227–230.
Series 5000 Model XTF5011 X–Ray Tube Information, Oxford Instruments Inc., Scotts Valley, GA, U.S.A., Jun. 1998.
Monolithic Polycapillary Lens Information, X–Ray Optical Systems, Inc., Albany, NY, U.S.A., Dec. 29, 1998. (web site: www.xos.com).
S. Di Fonzo et al., "Non–Destructive Determination of Local Strain with 100–Nanometre Spatial Resolution", *Nature*, vol. 403, Feb. 10, 2000. (web site: www.nature.com).

* cited by examiner

*Primary Examiner*—Robert H. Kim
*Assistant Examiner*—Hoon K. Song
(74) *Attorney, Agent, or Firm*—Hoffman, Wasson & Gitler (57) ABSTRACT

A method for measurement of critical dimensions includes irradiating a surface of a substrate with a beam of X-rays. A pattern of the X-rays scattered from the surface due to features formed on the surface is detected and analyzed to measure a dimension of the features in a direction parallel to the surface.

40 Claims, 5 Drawing Sheets

MEASUREMENT OF CRITICAL DIMENSIONS USING X-RAYS

FIELD OF THE INVENTION

The present invention relates generally to semiconductor manufacturing and process control, and specifically to measurements of critical dimensions of semiconductor device features.

BACKGROUND OF THE INVENTION

When microelectronic devices are produced on a semiconductor wafer, it is crucial that the critical dimensions of the devices be held within specified tolerances. Critical dimensions, in this context, refer to the widths of features, such as conductors, that are deposited on the wafer and the spacing between adjacent features. Deviations from the specified dimensions lead to performance and yield degradation. The manufacturing process must therefore be carefully monitored and controlled, in order to detect deviations as soon as they occur and to take corrective action to avoid the loss of costly wafers in process. For example, when a critical dimension in photoresist that has been deposited and etched on the wafer is found to be out of specification, it is possible to remove and reapply it.

A variety of systems and methods for measurement of critical dimensions are known in the art. Most microelectronic production facilities currently use optical metrology to monitor critical dimensions. As semiconductor devices become ever denser, however, with design rules of 0.25 $\mu$m and below, it becomes impossible for classical optical metrology systems to provide accurate results. Electron beam (e-beam) metrology has been suggested as an alternative, but e-beam systems also suffer from performance limitations.

A further problem in critical dimension measurements is the high aspect ratio and non-uniform width of features created on the semiconductor wafer. For example, in order to produce vias, a layer of photoresist is deposited on the wafer surface. The photoresist is exposed to ultraviolet radiation, hardened and then etched to form trenches, which are subsequently filled with metal. The photoresist is typically 0.7 to 1.2 $\mu$m thick, while the trenches are only 0.1 to 0.2 $\mu$m wide. (This width is the critical dimension of the vias.) Because of the etching process, the walls of the trenches tend to slope inward. The trenches are therefore wider at the top and narrower at the bottom, where they encounter the underlying wafer surface below the photoresist. It is the smaller width at the bottom of the trench that is most critical. Optical and e-beam metrology are not well suited for measuring this dimension, however, because of the high aspect ratio of the trenches.

X-ray reflectance and fluorescence measurements are commonly used to determine the thickness and composition of thin film layers, including particularly metal layers formed on semiconductor wafers. For example, U.S. Pat. No. 5,740,226, to Komiya et al., and U.S. Pat. No. 5,619,548, to Koppel, whose disclosures are incorporated herein by reference, describe film thickness measurements based on X-ray reflectometry.

Another method for thin film measurement using X-rays is described by Hayashi et al., in an article entitled "Refracted X-rays Propagating near the Surface under Grazing Incidence Condition," published in *Spectrochimica Acta*, Part B 54 (1999), pages 227–230, which is also incorporated herein by reference. The authors irradiated a silicon wafer having an organic thin film coating with X-rays incident at a grazing angle. They measured the energy of the X-rays that propagated along the surface of the wafer and discovered two peaks: one corresponding to refraction at the upper boundary between the thin film coating and the ambient air, and the other to refraction at the boundary between the coating and the wafer substrate. The energies of these peaks correspond to the critical energies of the respective boundaries. Below the critical energy, the X-rays are totally reflected from the boundary, while above the critical energy the X-rays pass through the boundary and are refracted. The critical energy for any given boundary depends on the angle of incidence of the X-rays and on the refractive indices of the materials separated by the boundary.

The methods of X-ray measurement mentioned above, as well as all other known X-ray methods, are limited to measurement of thickness or depth, i.e., of dimensions measured perpendicular to the plane of the wafer substrate. X-ray techniques known in the art do not generally have sufficient spatial resolution for use in measuring critical dimensions of feature width, i.e., dimensions of the features in a direction parallel to the substrate plane.

SUMMARY OF THE INVENTION

It is an object of some aspects of the present invention to provide improved methods and apparatus for measurement of critical dimensions of microelectronic devices, particularly during stages of wafer fabrication.

It is a further object of some aspects of the present invention to provide methods and apparatus capable of measuring the dimensions of microscopic features on a semiconductor wafer or other substrate having a high aspect ratio of height to width.

In preferred embodiments of the present invention, X-ray scattering from features on the surface of a substrate is detected in order to determine dimensions of the features, and particularly to measure the width of such features. Typically, the substrate comprises a semiconductor wafer, on which a test pattern is formed for the purpose of measuring critical dimensions of functional features of microelectronic devices in fabrication on the wafer. Preferably, the test pattern comprises a grating structure, made up of a periodic pattern of ridges, having attributes (such as height, width and spacing) similar to those of the functional features in question. When an X-ray beam irradiates the pattern, the resultant scattered radiation has a spatial modulation that is characteristic of the critical dimensions. A detection system senses and analyzes the modulation of the scattered radiation in order to determine the critical dimensions.

In some preferred embodiments of the present invention, the scattered radiation received by the detection system comprises reflected radiation. Preferably, the irradiating beam is well collimated and is incident on the surface at a grazing angle, nearly parallel to the surface of the substrate. Most preferably, the beam is incident in a direction whose projection on the surface is parallel to the ridges of the pattern. As a result, spatial modulation in the form of a "shadow" of the test pattern is imposed on the reflected radiation. The critical dimensions of the pattern are determined based on the characteristics of the modulation.

In one of these preferred embodiments, a collimator, which is used to collimate the irradiating beam, itself comprises a grating made of a pattern of ridges formed on a base. Preferably, the ridges on the collimator comprise metal ridges, having a period substantially equal to the period of the test pattern on the substrate under test. Reflection of the X-ray beam from the collimator at a grazing angle both collimates the beam and imposes on it the periodic pattern of the ridges. When the collimated beam is incident on the test substrate, an interference pattern is formed between the pattern imposed by the collimator and the test pattern. The detection system senses the interference pattern in order to determine the critical dimensions of the test pattern. Most preferably, the test substrate is translated relative to the collimator (or vice versa), causing the interference pattern to vary. The detection system senses this variation, which is then analyzed to determine the critical dimensions.

In other preferred embodiments of the present invention, the detection system captures a portion of the scattered radiation that is refracted at the surface of the substrate at an angle that is roughly parallel to the surface. The detection system analyzes the energy of X-ray photons that it captures and thus determines the critical energies for total external reflection at the surface, in a manner similar to that described in the above-mentioned article by Hayashi et al. Two different peaks are detected in the energy spectrum: one for the boundary between the ridges of the test pattern and the substrate, and the other for the boundary between the substrate and the ambient air, in the space between the ridges. The detection system analyzes the two peaks to determine the average width of the ridges relative to the intervening spaces.

Although preferred embodiments are described herein with reference to measurements of critical dimensions of features on semiconductor wafers, the principles of the present invention are similarly applicable to measuring the dimensions of microscopic features formed on substrates of other types. Furthermore, although these preferred embodiments are described with reference to particular types of test patterns and measurement modes, other methods of measuring critical width dimensions using X-rays will be apparent to those skilled in the art upon reading this description. All such methods are considered to be within the scope of the present invention.

There is therefore provided, in accordance with a preferred embodiment of the present invention, a method for measurement of critical dimensions, including:

irradiating a surface of a substrate with a beam of X-rays;

detecting a pattern of the X-rays scattered from the surface due to features formed on the surface; and analyzing the pattern to measure a dimension of the features in a direction parallel to the surface.

Preferably, irradiating the surface includes collimating the beam of X-rays that is to irradiate the surface.

Further preferably, the features formed on the surface include a periodic structure on the substrate having a predetermined period, and collimating the beam of X-rays includes imposing on the beam a spatial modulation, and detecting the pattern includes observing an interference pattern generated due to interaction of the spatial modulation with the periodic structure. Most preferably, imposing the spatial modulation includes modulating the beam with a spatial period substantially equal to the predetermined period of the structure. Additionally or alternatively, the periodic structure on the substrate includes a first grating structure, and imposing the spatial modulation includes reflecting the beam from a second grating structure, wherein analyzing the pattern includes observing changes in the interference pattern as one of the first and second grating structures is translated relative to the other.

Additionally or alternatively, the features include a periodic structure, and wherein detecting the pattern includes detecting a modulation of the reflected X-rays due to the periodic structure. Preferably, the periodic structure includes a grating made up of a plurality of ridges oriented parallel to a grating axis, and irradiating the surface includes directing the beam of X-rays toward the surface such that a projection of the beam on the surface is substantially parallel to the grating axis. Further additionally or alternatively, the periodic structure includes a grating made up of a plurality of ridges oriented parallel to a grating axis, and irradiating the surface includes directing the beam of X-rays toward the surface such that a projection of the beam on the surface is substantially perpendicular to the grating axis.

Still further additionally or alternatively, the periodic structure includes a thin film layer formed on the substrate and etched to form the periodic structure. Preferably, the thin film layer is etched to form ridges while exposing an area of the surface of the substrate between the ridges, and detecting the pattern includes detecting variations in the scattered X-rays indicative of a width of the exposed area.

Preferably, detecting the pattern of the X-rays includes detecting a variation in the scattered X-rays associated with total external reflection from an area of the surface. Further preferably, the substrate includes a first material having a first refractive index, and wherein the features include a second material, having a second refractive index different from the first refractive index, and detecting the variation includes finding a difference between the total external reflection of X-rays incident on a boundary between the first and second materials and of X-rays incident on the first material in an area of the surface on which the second material is substantially absent. More preferably, irradiating the surface includes irradiating the surface near a critical angle of the first material, such that the beam of X-rays is reflected from the area of the surface on which the second material is substantially absent, but is substantially not reflected from the boundary between the first and second materials. Most preferably, finding the difference includes detecting a spatial modulation of X-rays reflected from the surface due to the total external reflection.

Additionally or alternatively, finding the difference includes detecting a distinction between the critical energies for total external reflection from the boundary between the first and second materials and from the area of the surface on which the second material is substantially absent. Preferably, detecting the distinction includes detecting X-rays refracted parallel to the surface, and analyzing the pattern includes analyzing the detected X-rays to find the critical energies.

Still further additionally or alternatively, detecting the pattern of the X-rays includes detecting a variation in refraction of X-rays at the surface.

Preferably, the substrate includes a semiconductor wafer, and the features formed on the surface include photoresist deposited on the surface.

There is also provided, in accordance with a preferred embodiment of the present invention, apparatus for measurement of critical dimensions, including:

an X-ray source, configured to irradiate a surface of a substrate with a beam of X-rays;

a detector, adapted to detect a pattern of the X-rays scattered from the surface due to features formed on the surface and to generate a signal responsive to the pattern; and a processor, coupled to receive and analyze the signal so as to measure a dimension of the feature in a direction parallel to the surface.

Preferably, the X-ray source includes a collimator, adapted to collimate the beam of X-rays that is to irradiate the surface.

In a preferred embodiment, the apparatus includes a translation device, adapted to shift one of the first and second gratings relative to the other, wherein the processor is adapted to analyze changes in the interference pattern as the one of the first and second gratings is shifted.

There is additionally provided, in accordance with a preferred embodiment of the present invention, a collimator, including:

a substrate; and a grating structure formed on the substrate, the structure including a plurality of parallel ridges aligned parallel to an axis of the grating, so as to collimate a beam of X-rays incident on the substrate at a grazing angle.

Preferably, the substrate includes a first material, which reflects the X-rays incident at the grazing angle, and wherein the ridges include a second material, which absorbs the X-rays. Most preferably, the first material includes a semiconductor material, and the second material includes a metal.

The present invention will be more fully understood from the following detailed description of the preferred embodiments thereof, taken together with the drawings in which:

DETAILED DESCRIPTION OF PREFERRED EMBODIMENTS

Figure 1:
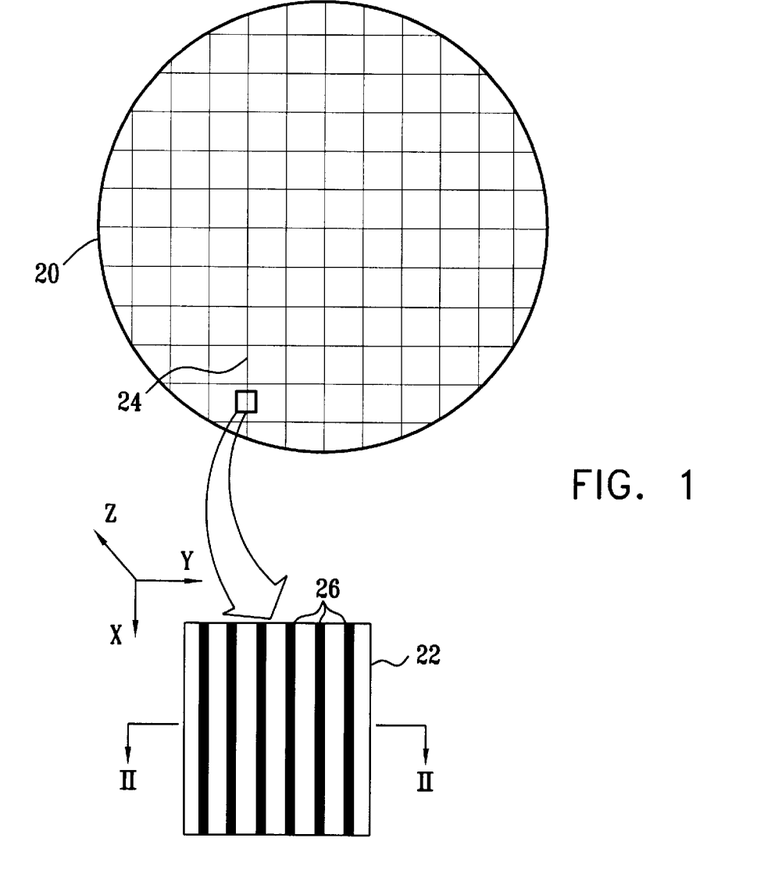
FIG. 1 is a schematic top view of a semiconductor wafer and a detail of a test pattern on the wafer, in accordance with a preferred embodiment of the present invention.
Figure 2:
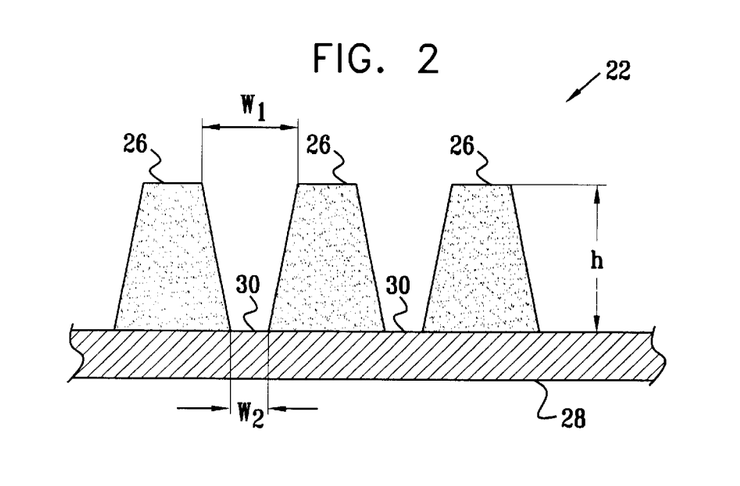
FIG. 2 is a schematic, cross-sectional view of the test pattern of FIG. 1, taken along a line II—II.

Reference is now made to FIGS. 1 and 2, which schematically illustrate a semiconductor wafer 20 and details of a test pattern 22 formed thereon, in accordance with a preferred embodiment of the present invention. FIG. 1 is a top view of the wafer, with the test pattern shown enlarged in an inset. FIG. 2 is an enlarged, cross-sectional view of the test pattern, taken along line II—II in FIG. 1. A set of Cartesian axes is shown in FIG. 1 for later reference, wherein the wafer will be considered to be in the X-Y plane.

Although the preferred embodiments described hereinbelow relate specifically to wafer 20, She principles of the present invention may similarly be applied to other patterned objects.

Test pattern 22 preferably comprises a grating of parallel ridges 26. For convenience in the description that follows, the ridges are assumed to be aligned along the X-direction. The test pattern is preferably formed on a scribe line 24 between adjacent dice on wafer 20, so as to minimize the loss of useful space on the wafer. Typically, ridges 26 are formed by the same processes of material deposition, photolithography and etching as are functional circuit features on the wafer that pattern 22 is intended to test. In the example of FIGS. 1 and 2, ridges 26 comprise photoresist, which is deposited on the wafer surface. The photoresist is masked and etched to form gaps 30 between the ridges, just as it is on the remainder of the wafer, as a step in producing the circuit features thereon. Within gaps 30, an underlying substrate layer 28 is exposed. Layer 28 typically comprises an oxide or metal layer, or it may comprise the silicon wafer substrate itself.

Test pattern 22 is designed to have the same critical dimensions as the functional circuit features on wafer 20, including particularly the widths of ridges 26 and of gaps 30 between the ridges. In modern devices, the height h of ridges 26 is typically five to six times the width of gaps 30. Because of this high aspect ratio and the nature of the chemical etching process used to create gaps 30, the widths of the gaps are generally not uniform. Rather, the widths tend to have a larger dimension $W_1$ at the upper surface of ridges 26, and a smaller dimension $W_2$ at the bottom of the gaps. Dimension $W_2$ tends to be the most critical dimension and the most difficult to measure using optical or e-beam techniques. The methods of measurement described hereinbelow focus on $W_2$.

Figure 3:
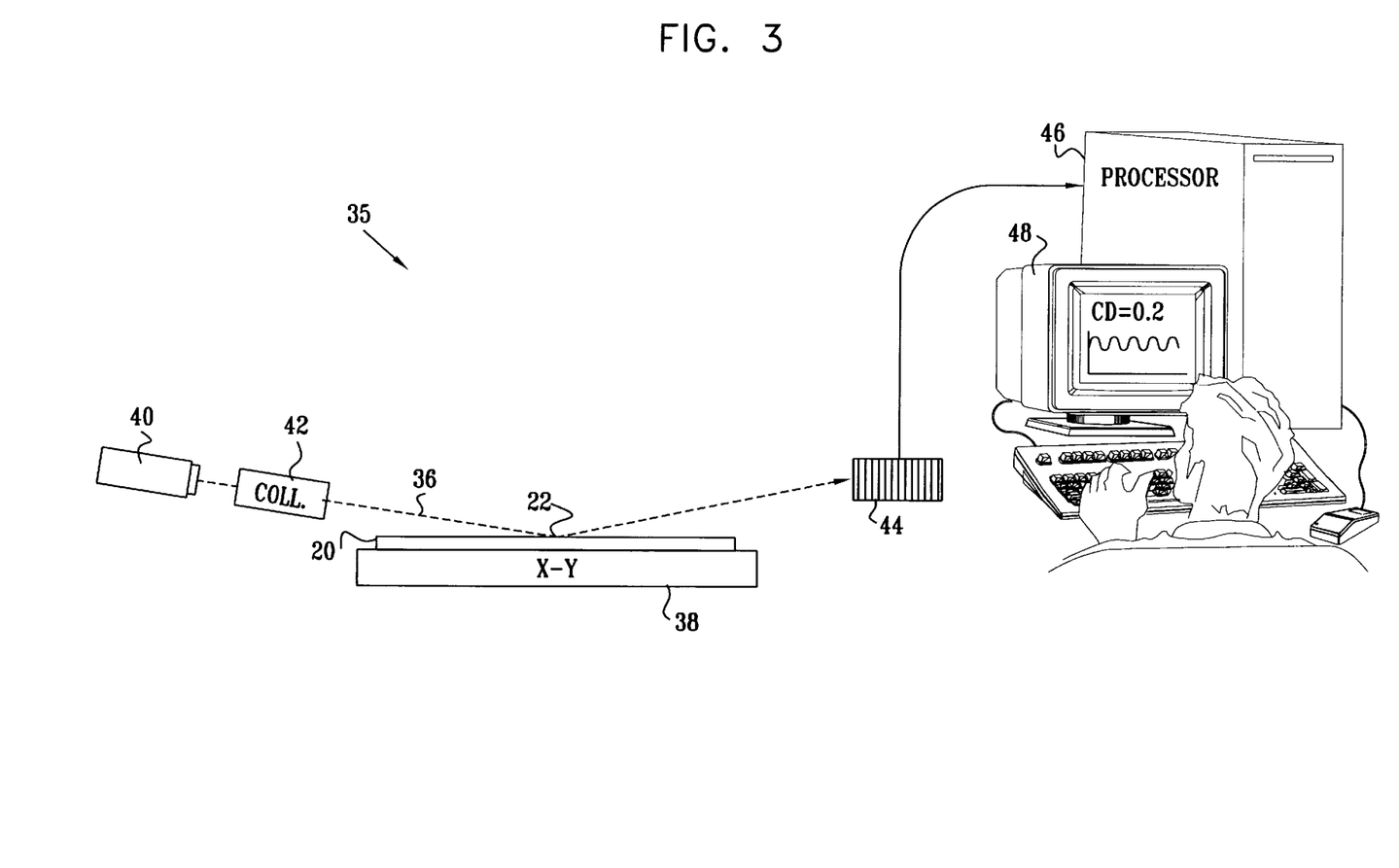
FIG. 3 is a schematic, pictorial illustration of apparatus for measurement of critical dimensions using X-rays, in accordance with a preferred embodiment of the present invention.

FIG. 3 is a schematic, pictorial illustration of a system 35 for measurement of critical dimensions on wafer 20, in accordance with a preferred embodiment of the present invention. An X-ray source 40 emits a beam 36 of X-rays, which is collimated by an optic 42 and directed onto test pattern 22 on wafer 20. X-ray source 24 preferably comprises an X-ray tube, such as an XTF 5011 tube produced by Oxford Instruments, Inc., of Scotts Valley, Calif. Optionally, optic 42 also focuses, filters and/or monochromatizes the radiation, using any suitable methods and devices known in the art, depending on the characteristics of the X-ray source and the demands of the measurement being performed. Thus, although optic 42 is shown in FIG. 3 as a single unit, it optionally comprises two or more separate elements for focusing, filtering and/or monochromatizing the radiation. It is noted, however, that focusing is optional, and the key requirement in this embodiment is that the beam be collimated. For focusing, the optic preferably comprises a monolithic polycapillary lens, such as those produced by X-Ray Optical Systems, Inc., of Albany, N.Y., which collects the X-rays and focuses them to a spot on pattern 22. Alternatively, optic 42 comprises a monocapillary optic and/or X-ray collimating pinholes, or any other: suitable collimating means known in the art. Further alternatively, the optic comprises a curved monochromator, as described in the above-mentioned U.S. Pat. No. 5,619,548, for example.

Radiation scattered from pattern 22 is collected by an X-ray detector 44. Preferably, detector 44 comprises an array of X-ray detecting elements, such as a CCD array. Alternatively, other types of X-ray detectors may be used in this context, as described further hereinbelow. The array detector is advantageous in being able to receive and measure the scattered radiation over a wide angular range substantially without motion of the detector. The scattered radiation exhibits a pattern of modulation that is characteristic of the critical dimensions of ridges 26 and gaps 30. Detector 44 outputs a signal responsive to the flux of X-ray photons incident on the detector. The signal is received and analyzed by a processor 46, preferably a general-purpose computer equipped with suitable signal processing hardware and software. The processor preferably analyzes the pattern of modulation of the scattered radiation and outputs a measurement of selected critical dimensions of pattern 22, most preferably together with a plot of the pattern, to an output device, such as a display 48.

Figure 4:
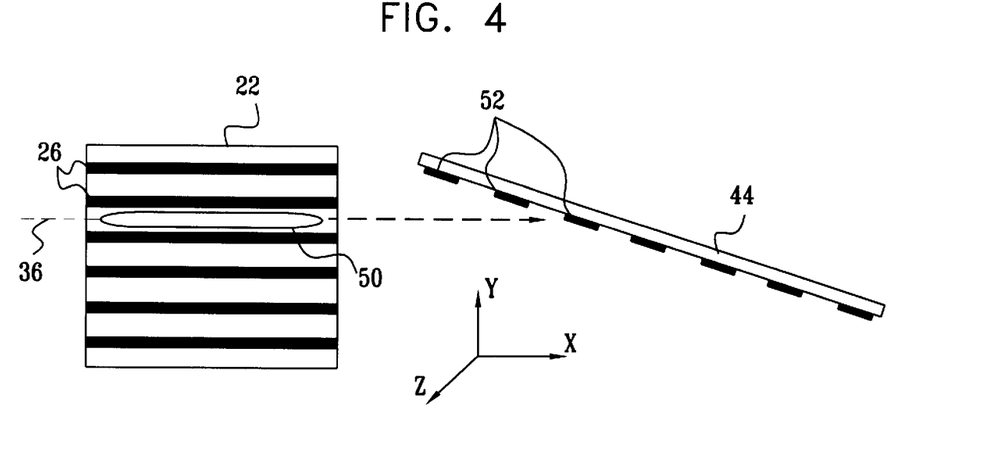
FIG. 4 is a schematic top view of a detail of the apparatus of FIG. 3, showing particularly a test pattern on a wafer and a detector array used in the apparatus, in accordance with a preferred embodiment of the present invention.

FIG. 4 is a schematic top view of pattern 22 and detector 44, illustrating a preferred embodiment of the present invention. X-ray beam 36 is preferably focused by collimation to a small spot 50, as shown in the figure, most preferably with a beam diameter on the order of the spacing of ridges 36, i.e., less than 1 μm. Alternatively, a wider beam may be used if it is sufficiently well-collimated. Preferably the angular divergence of the beam is less than the angular width of ridges 26. (A particular example of a wide beam used for this purpose is described hereinbelow with reference to FIGS. 6 and 7.) The beam strikes wafer 20 at a grazing angle, giving an elongated "footprint" of the beam on pattern 22, as shown in the figure.

Returning to FIG. 2, it will be observed that X-ray beam 36 may be incident on the surface of substrate 28 both within gaps 30 and within ridges 26. Typically, the beam spreads over at least one gap and one ridge. Assuming the ridges to be made of an organic photoresist, they will have a substantially smaller refractive index to the X-rays than will the ambient air in gaps 30. The refractive index of substrate 28 is still lower than that of the photoresist. Therefore, the critical angle for total external reflection of the X-rays from the surface of the substrate within ridges 26 is substantially lower than that in gaps 30.

Representative values of the critical angle at an X-ray beam energy of about 8 keV are 3.9 mrad for the air/substrate boundary and 3.1 mrad for the ridge/substrate boundary. (These figures assume the substrate to comprise silicon, with refractive index $n_{sub}=1-7.6\times10^{-6}$, and the organic photoresist to have a typical refractive index of $n_1=1-4.6\times10^{-6}$). Beam 36 is preferably directed at an angle of about 3.4 mrad relative to the surface. The beam is thus reflected from substrate 28 within gaps 30, but passes into the substrate when it strikes the substrate inside ridges 26. Because low-energy photons undergo total reflection within both gaps 30 and ridges 26, beam 36 is preferably high-pass filtered in order to prevent the low-energy photons from reaching detector 44 and reducing the contrast of the measurement. A metal foil filter can be used for this purpose. Other X-ray energies and angles may be used, depending on the types of materials present in pattern 22 and substrate 28.

As a result of the differences in critical angles, the profile of the beam reflected from pattern 22 is spatially modulated with a "shadow" image of the pattern. The period of the shadow pattern is roughly equal to the spacing of ridges 26, while the width of the peaks in the pattern is roughly equal to the width dimension $W_2$ of gaps 30. This ability to sense the critical dimension at the wafer surface is unique to the X-ray based methods of the present invention, as opposed to optical and e-beam methods, which measure the dimension $W_1$ at the upper end of gaps 30.

Detector 44 in this embodiment comprises an array of sensing elements 52, such as a CCD array. Because of the limitations of detector technology at present, elements 52 typically have a pitch of roughly 1 μm. Detector 44 is therefore preferably inclined at an angle of about 50 mrad relative to the long axis of ridges 26, giving an effective pitch along the Y-axis of about 50 nm. The detector is thus able to sense the modulation of the reflected X-rays and to pass the resultant signal to processor 46 for analysis.

Figure 5:
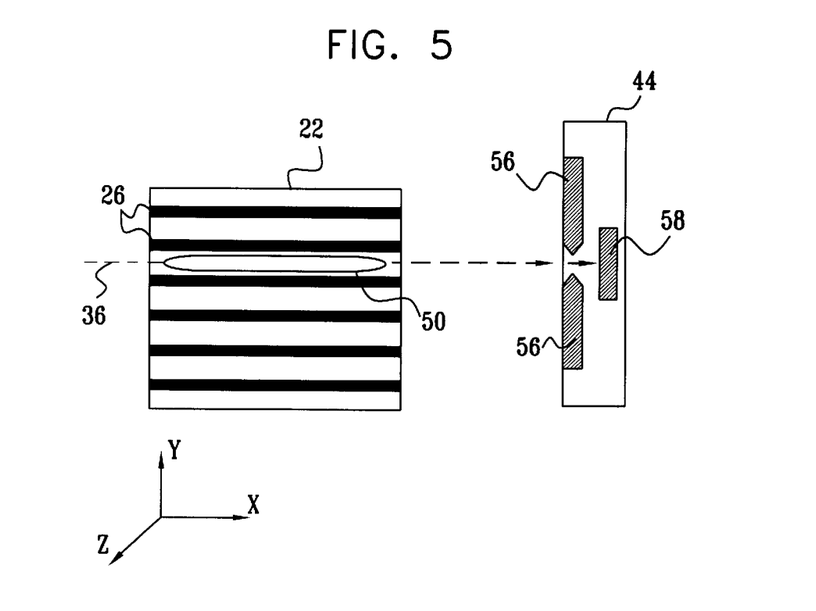
FIG. 5 is a schematic top view of a detail of the apparatus of FIG. 3, showing the test pattern on the wafer and a detector device used in the apparatus, in accordance with another preferred embodiment of the present invention.

FIG. 5 is a schematic top view of pattern 22 and detector 44, illustrating another preferred embodiment of the present invention. This embodiment is substantially similar to the embodiment of FIG. 4, except for the configuration of the detector. In the embodiment of FIG. 5, detector 44 comprises an X-ray sensing element 58 masked by a slit 56. The slit is narrowed as required to provide the required spatial resolution. Either the slit or the entire detector is scanned in the Y-direction to cover the entire pattern of modulation of the reflected X-rays. Optionally, multiple detectors of this sort are used to cover the pattern more rapidly.

Figure 6:
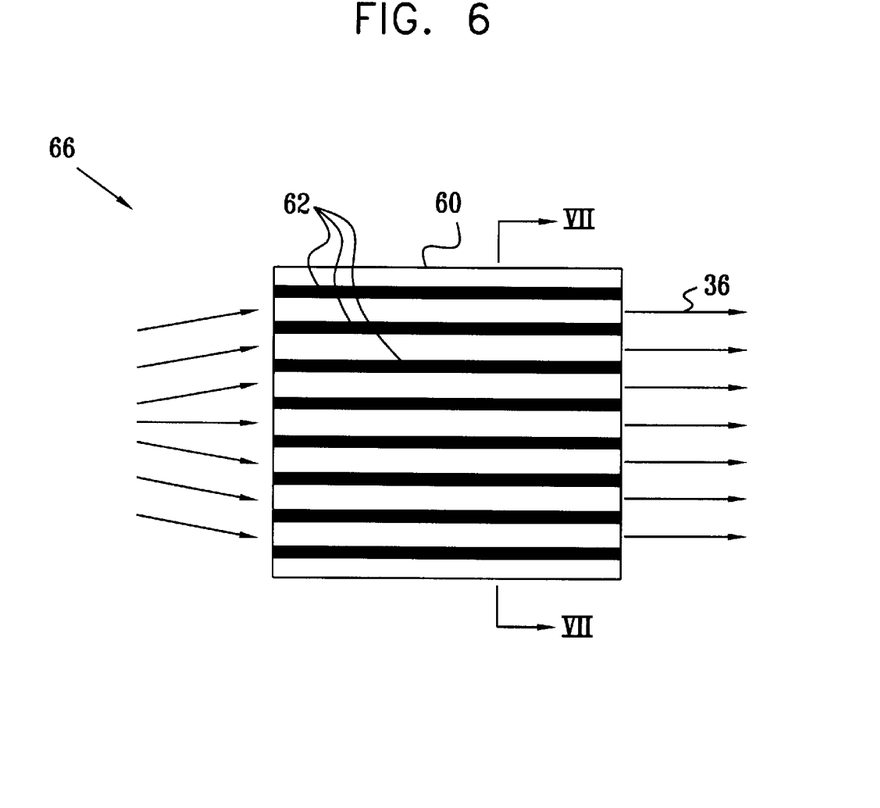
FIG. 6 is a schematic top view of a collimator for use in the system of FIG. 3, in accordance with a preferred embodiment of the present invention.
Figure 7:
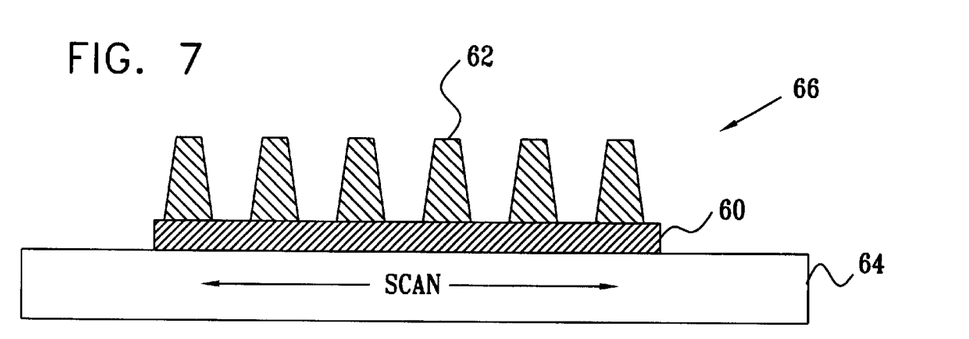
FIG. 7 is a schematic, cross-sectional view of the collimator of FIG. 6, taken along a line VII—VII.

FIGS. 6 and 7 schematically illustrate a special-purpose collimator 66, used in the place of optic 42 (FIG. 3), in accordance with a preferred embodiment of the present invention. FIG. 6 is a top view of the collimator, while FIG. 7 is an enlarged, cross-sectional view seen along a line VII—VII in FIG. 6. The collimator comprises a grating of ridges 62 formed on a substrate 60. The ridges comprise an X-ray absorbing material, such as copper, with a height of about one to several μm and a pitch (center-to-center spacing) equal to the pitch of ridges 26 in pattern 22. X-rays from source 40 are incident on collimator 66 at a grazing angle. As a result of interaction of the X-rays with ridges 62, beam 36 is reflected from the collimator with a high degree of collimation and with an amplitude pattern that is spatially modulated with a period equal to the pitch of the ridges.

When beam 36 from collimator 66 is incident on pattern 22, interference occurs between the existing spatial modulation of the beam and further modulation imposed, at the same spatial period, by the pattern on the wafer. Collimator 66 is preferably mounted on a scanning table 64, which scans the collimator in the Y-direction in order to vary the phase of the spatial modulation of the collimated beam relative to pattern 22. Alternatively or additionally, wafer 20 is mounted on a scanner 38 (FIG. 3). Detector 44 measures the changes in amplitude of the X-rays reflected from pattern 22 as the collimator and pattern are translated relative to one another. Mutual alignment between the grating on collimator 66 and the ridges of pattern 22 must typically be carefully maintained. The shape and height of the peak in the reflected amplitude are indicative of the critical dimension $W_2$ of gaps 30. Typically only a single detector element is required for this purpose, rather than an array as in FIG. 4.

Figure 8:
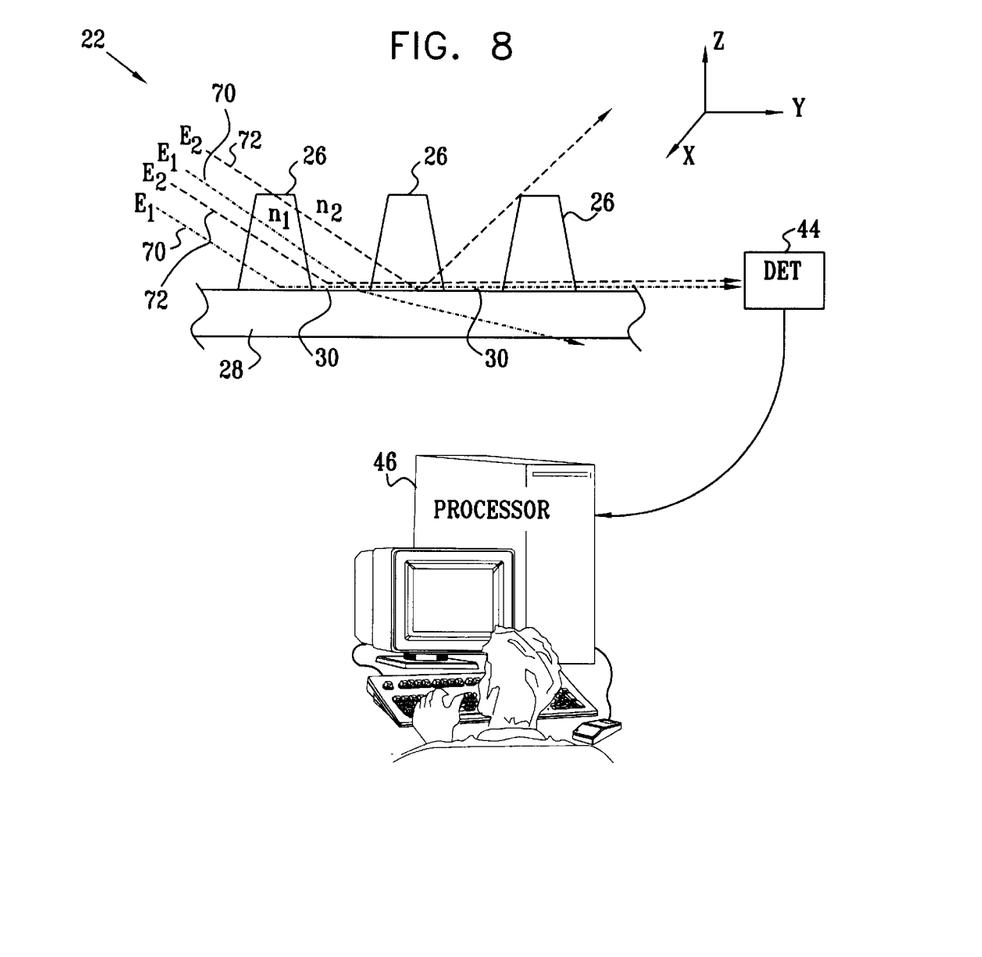
FIG. 8 is a schematic side view showing details of a test pattern and detector used in measurement of critical dimensions, in accordance with another preferred embodiment of the present invention.

FIG. 8 is a schematic side view of pattern 22 in system 35, illustrating another preferred embodiment of the present invention. This embodiment measures the average value of the critical dimension using the principle described in the above-mentioned article by Hayashi et al., wherein for a given angle of incidence of X-rays on the surface of substrate 28, there is a critical energy of the X-rays at which the beam is refracted parallel to the surface. Assuming the organic material of ridges 26 to have a refractive index $n_1$, and the air in gaps 30 to have a refractive index $n_2$ ($n_1 > n_2$), the critical energy $E_1$ for the portions of the substrate surface within ridges 26 will be different from the critical energy $E_2$ within gaps 30, with $E_1 > E_2$. On the basis of the results described in the article, for refraction at 0.04°, $E_1 \approx 16.5$ keV, and $E_2 \approx 14.5$ keV. Thus, photons 70 at energy $E_1$ are refracted parallel to the substrate surface when they are incident on substrate 28 within ridges 26 but pass into the substrate when they are incident in gaps 30. On the other hand, photons 72 at energy $E_2$ are refracted parallel to the surface when they are incident on substrate 28 within gaps 30 but reflect off the surface within ridges 26.

Detector 44 in this embodiment is positioned in the plane of wafer 20, so as to capture the photons refracted along the wafer surface. In FIG. 8, for clarity of illustration, the direction of incidence of photons 70 and 72 is generally perpendicular to the direction of ridges 26. In practice, however, the photons are preferably directed generally parallel to the ridges, as shown in FIGS. 4 and 5. Detector 44 preferably comprises a silicon diode or a high-sensitivity Si—Li detector, as are known in the art of X-ray analysis. For each incident photon, the detector generates a pulse that is proportional in amplitude to the energy of the photon. Processor 46 analyzes the pulse amplitudes to generate an energy spectrum of the radiation incident on detector 44.

Figure 9:
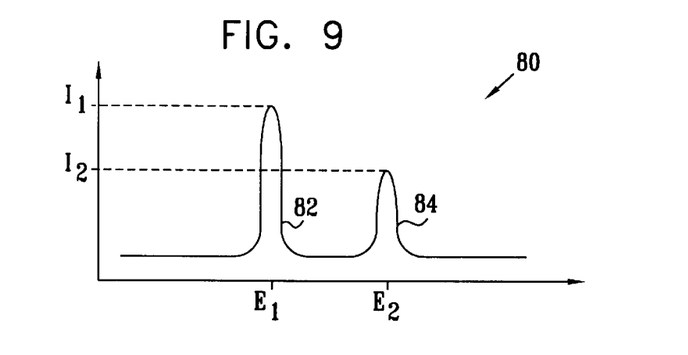
FIG. 9 is a schematic plot of an energy spectrum of X-rays received by the detector of FIG. 8.

FIG. 9 is a schematic plot 80 of a typical spectrum generated by processor 46 in the configuration of FIG. 8. The plot exhibits peaks 82 and 84, at critical energies $E_1$ and $E_2$, respectively. The amplitudes of the peaks, $I_1$ and $I_2$, represent the number of X-ray photons that were incident at each of the energies. The ratio of the two amplitudes is generally proportional to the average ratio of the width of ridges 26 at their base to the lower width $W_2$ of gaps 30. Too large a ratio $I_1/I_2$ indicates that the gaps are too narrow.

While the preferred embodiments described above are directed mainly to measurement of critical width dimensions (i.e., measurements in the X-Y plane), these width measurement techniques may be combined in a straightforward and useful manner with techniques that use X-rays, as well, to measure feature depth or thickness (in the Z-direction). Suitable methods for measurement of the thickness and composition of thin film layers and semiconductor device features are described particularly in U.S. patent applications Ser. Nos. 09/408,894 and 09/409,046. These applications are assigned to the assignee of the present patent application, and their disclosures are incorporated herein be reference. Alternatively or additionally, other methods of X-ray measurement, as described in the Background of the Invention or as are otherwise known in the art, may also be used in combination with the methods and apparatus of the present invention.

Although preferred embodiments are described hereinabove with reference to measurements of critical dimensions of features on semiconductor wafer 20, and particularly of features etched in photoresist on the wafer, the principles of the present invention are similarly applicable to measuring features at other stages of semiconductor device fabrication, as well as measuring the dimensions of microscopic features formed on substrates of other types. Furthermore, although these embodiments are described with reference to an exemplary test pattern 22 and certain preferred modes of measurement, other patterns and modes for critical dimension measurement using X-rays will be apparent to those skilled in the art. It will thus be appreciated that the preferred embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

What is claimed is:

1. A method for measurement of critical dimensions, comprising:
    irradiating a surface of a substrate with a beam of X-rays;
    detecting a pattern of the X-rays scattered from the surface due to features formed on the surface; and
    analyzing the pattern to measure a dimension of the features in a direction parallel to the surface.

2. A method according to claim 1, wherein irradiating the surface comprises collimating the beam of X-rays that is to irradiate the surface.

3. A method according to claim 2, wherein the features formed on the surface comprise a periodic structure on the substrate having a predetermined period, and
    wherein collimating the beam of X-rays comprises imposing on the beam a spatial modulation, and
    wherein detecting the pattern comprises observing an interference pattern generated due to interaction of the spatial modulation with the periodic structure.

4. A method according to claim 3, wherein imposing the spatial modulation comprises modulating the beam with a spatial period substantially equal to the predetermined period of the structure.

5. A method according to claim 3, wherein the periodic structure on the substrate comprises a first grating structure, and wherein imposing the spatial modulation comprises reflecting the beam from a second grating structure.

6. A method according to claim 5, wherein analyzing the pattern comprises observing changes in the interference pattern as one of the first and second grating structures is translated relative to the other.

7. A method according to claim 1, wherein the features comprise a periodic structure, and wherein detecting the pattern comprises detecting a modulation of the reflected X-rays due to the periodic structure.

8. A method according to claim 7, wherein the periodic structure comprises a grating made up of a plurality of ridges oriented parallel to a grating axis, and
    wherein irradiating the surface comprises directing the beam of X-rays toward the surface such that a projection of the beam on the surface is substantially parallel to the grating axis.

9. A method according to claim 7, wherein the periodic structure comprises a grating made up of a plurality of ridges oriented parallel to a grating axis, and
    wherein irradiating the surface comprises directing the beam of X-rays toward the surface such that a projection of the beam on the surface is substantially perpendicular to the grating axis.

10. A method according to claim 7, wherein the periodic structure comprises a thin film layer formed on the substrate and etched to form the periodic structure.

11. A method according to claim 10, wherein the thin film layer is etched to form ridges while exposing an area of the surface of the substrate between the ridges, and
    wherein detecting the pattern comprises detecting variations in the scattered X-rays indicative of a width of the exposed area.

12. A method according to claim 1, wherein detecting the pattern of the X-rays comprises detecting a variation in the scattered X-rays associated with total external reflection from an area of the surface.

13. A method according to claim 12, wherein the substrate comprises a first material having a first refractive index, and wherein the features comprise a second material, having a second refractive index different from the first refractive index, and wherein detecting the variation comprises finding a difference between the total external reflection of X-rays incident on a boundary between tie first and second materials and of X-rays incident on the first material in an area of the surface on which the second material is substantially absent.

14. A method according to claim 13, wherein irradiating the surface comprises irradiating the surface near a critical angle of the first material, such that the beam of X-rays is reflected from the area of the surface on which the second material is substantially absent, but is substantially not reflected from the boundary between the first and second materials.

15. A method according to claim 14, wherein finding the difference comprises detecting a spatial modulation of X-rays reflected from the surface due to the total external reflection.

16. A method according to claim 13, wherein finding the difference comprises detecting a distinction between the critical energies for total external reflection from the boundary between the first and second materials and from the area of the surface on which the second material is substantially absent.

17. A method according to claim 16, wherein detecting the distinction comprises detecting X-rays refracted parallel to the surface, and
wherein analyzing the pattern comprises analyzing the detected X-rays to find the critical energies.

18. A method according to claim 1, wherein detecting the pattern of the X-rays comprises detecting a variation in refraction of X-rays at the surface.

19. A method according to claim 1, wherein the substrate comprises a semiconductor wafer.

20. A method according to claim 19, wherein the features formed on the surface comprise photoresist deposited on the surface.

21. Apparatus for measurement of critical dimensions, comprising:
an X-ray source, configured to irradiate a surface of a substrate with a beam of X-rays;
a detector, adapted to detect a pattern of the X-rays scattered from the surface due to features formed on the surface and to generate a signal responsive to the pattern; and
a processor, coupled to receive and analyze the signal so as to measure a dimension of the feature in a direction parallel to the surface.

22. Apparatus according to claim 21, wherein the X-ray source comprises a collimator, adapted to collimate the beam of X-rays that is to irradiate the surface.

23. Apparatus according to claim 22, wherein the features formed on the surface comprise a periodic structure on the substrate having a predetermined period, and
wherein the collimator is further adapted to impose on the beam a spatial modulation, and the pattern comprises an interference pattern generated due to interaction of the spatial modulation with the periodic structure.

24. Apparatus according to claim 23, wherein the spatial modulation has a spatial period substantially equal to the predetermined period of the structure.

25. Apparatus according to claim 23, wherein the periodic structure on the substrate comprises a first grating structure, and wherein the collimator comprises a second grating structure.

26. Apparatus according to claim 25, and comprising a translation device, adapted to shift one of the first and second gratings relative to the other, wherein the processor is adapted to analyze changes in the interference pattern as the one of the first and second gratings is shifted.

27. Apparatus according to claim 21, wherein the features comprise a periodic structure, and wherein the pattern comprises a modulation of the reflected X-rays due to the periodic structure.

28. Apparatus according to claim 27, wherein the periodic structure comprises a grating made up of a plurality of ridges oriented parallel to a grating axis, and
wherein the X-ray source is configured to irradiate the surface such that a projection of the beam on the surface is substantially parallel to the grating axis.

29. Apparatus according to claim 27, wherein the periodic structure comprises a grating made up of a plurality of ridges oriented parallel to a grating axis, and
wherein the X-ray source is configured to irradiate the surface such that a projection of the beam on the surface is substantially perpendicular to the grating axis.

30. Apparatus according to claim 27, wherein the periodic structure comprises a thin film layer formed on the substrate and etched to form the periodic structure.

31. Apparatus according to claim 30, wherein the thin film layer is etched to form ridges while exposing an area of the surface of the substrate between the ridges, and wherein the pattern comprises variations in the scattered X-rays indicative of a width of the exposed area.

32. Apparatus according to claim 21, wherein the pattern of the X-rays comprises a variation in the scattered X-rays associated with total external reflection from an area of the surface.

33. Apparatus according to claim 22, wherein the substrate comprises a first material having a first refractive index, and wherein the features comprise a second material, having a second refractive index different from the first refractive index, and
wherein the variation arises from a difference between the total external reflection of X-rays incident on a boundary between the first and second materials and of X-rays incident on the first material in an area of the surface on which the second material is substantially absent.

34. Apparatus according to claim 33, wherein the X-ray source is aligned to irradiate the surface near a critical angle of the first material, such that the beam of X-rays is reflected from the area of the surface on which the second material is substantially absent, but substantially not from the boundary between the first and second materials.

35. Apparatus according to claim 34, wherein the detector is adapted to detect a spatial modulation of X-rays reflected from the surface due to the total external reflection.

36. Apparatus according to claim 33, wherein the processor is adapted to find a distinction between the critical energies for total external reflection from the boundary between the first and second materials and from the area of the surface on which the second material is substantially absent.

37. Apparatus according to claim 36, wherein the detector is positioned to detect X-rays refracted parallel to the surface, and the processor is adapted to analyze the detected X-rays to find the critical energies.

38. Apparatus according to claim 21, wherein the pattern arises due to a variation in refraction of X-rays at the surface.

39. Apparatus according to claim 21, wherein the substrate comprises a semiconductor wafer.

40. Apparatus according to claim 39, wherein the features formed on the surface comprise photoresist deposited on the surface.

* * * * *